United States Patent [19]

Wootton

[11] 4,147,796
[45] Apr. 3, 1979

[54] 1-(3-HYDROXYALK-1-yl)-5-(CARBOXYALK-YL)HYDANTOIN DERIVATIVES

[75] Inventor: Gordon Wootton, Sawbridgeworth, England

[73] Assignee: Beecham Group Limited, Great Britain

[21] Appl. No.: 915,164

[22] Filed: Jun. 14, 1978

Related U.S. Application Data

[63] Continuation-in-part of Ser. No. 858,562, Dec. 8, 1977, abandoned.

[30] Foreign Application Priority Data

Dec. 18, 1976 [GB] United Kingdom ............... 52955/76
Jul. 20, 1977 [GB] United Kingdom ............... 30369/77

[51] Int. Cl.² ................. A61K 31/415; C07D 233/78; C07D 233/86
[52] U.S. Cl. ................................. 424/273 R; 548/313
[58] Field of Search .................... 548/313; 424/273 R

[56] References Cited

U.S. PATENT DOCUMENTS

| | | | |
|---|---|---|---|
| 2,290,281 | 7/1942 | Henze | 548/313 |
| 2,436,851 | 3/1948 | Businger | 548/313 |
| 2,955,057 | 10/1960 | Gagliardi et al. | 548/313 |
| 3,246,002 | 4/1966 | Gagliardi et al. | 260/299 |
| 3,256,247 | 6/1966 | Gagliardi et al. | 548/313 |
| 3,576,858 | 4/1971 | Mizoguchi et al. | 548/313 |
| 3,798,233 | 3/1974 | Akiba et al. | 548/313 |
| 4,089,860 | 5/1978 | Merten et al. | 548/313 |

FOREIGN PATENT DOCUMENTS

| | | | |
|---|---|---|---|
| 2539730 | 3/1977 | Fed. Rep. of Germany | 548/313 |
| 1273868 | 9/1961 | France | 548/313 |

OTHER PUBLICATIONS

Dakin, Amer. Chem. Journal, 1910, vol. 44, pp. 48–60.
Ware, Chem. Rev., 1950, vol. 46, pp. 406–407.

Primary Examiner—Natalie Trousof
Assistant Examiner—Natalia Harkaway
Attorney, Agent, or Firm—Jacobs & Jacobs

[57] ABSTRACT

A compound of formula (I):

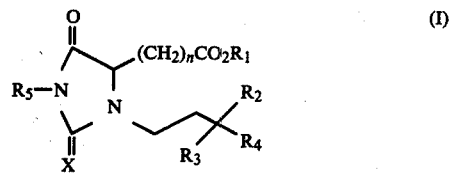

wherein:
X is O or S;
n is 1 to 8;
$R_1$ is hydrogen, or $CO_2R_1$ represents an ester group in which the $R_1$ moiety contains from 1–12 carbon atoms;
$R_2$ is hydrogen, $C_{1-4}$ alkyl, or phenyl;
$R_3$ is hydroxy or protected hydroxy,
$R_4$ is hydrogen, $C_{1-9}$ alkyl, $C_{3-8}$ cycloalkyl, $C_{3-8}$ cyclo alkyl-$C_{1-6}$ alkyl, phenyl, phenyl $C_{1-6}$ alkyl, naphthyl, naphthyl-$C_{1-6}$-alkyl, any of which phenyl or naphthyl moieties may be substituted by one or more halogen, trifluoromethyl, $C_{1-6}$ alkyl, hydroxy, $C_{1-6}$ alkoxy, phenyl $C_{1-6}$ alkoxy or nitro groups; or
$R_2$ and $R_4$ taken with the carbon atom to which they are joined represent a $C_{5-8}$ cycloalkyl group;
$R_5$ is $C_{1-6}$ alkyl, $C_{1-6}$ alkyl substituted by a nitro, hydroxy, $C_{1-6}$ alkoxy, $CO_2A$, $(CO_2A)_2$, CN or halogen group, $C_{5-8}$ cycloalkyl, phenyl, phenyl, phenyl-$C_{1-6}$ alkyl, phenyl-$C_{3-6}$ cycloalkyl, any of which phenyl moieties may be substituted by one or more halogen, trifluoromethyl, $C_{1-6}$ alkyl, $C_{1-6}$ alkoxy or nitro groups; or a group $CO_2A$; in $R_5$ when present A is hydrogen or $CO_2A$ represents an ester group in which the A moiety contains from 1 to 12 carbon atoms; and salts thereof; has useful pharmacological activity.

32 Claims, No Drawings

1-(3-HYDROXYALK-1-yl)-5-(CARBOXYALKYL)-HYDANTOIN DERIVATIVES

CROSS-REFERENCE TO RELATED APPLICATION

This is a continuation-in-part of Ser. No. 858,562 filed Dec. 8, 1977 now abandoned.

This invention relates to novel compounds having pharmacological activity, to a process for their preparation, to intermediates useful in that process and to pharmaceutical compositions containing them.

Offenlegungsschrift No. 2323193 discloses that pyrazolidine derivatives of the formula (I)':

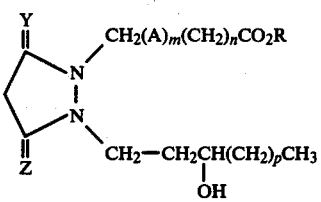

wherein A is CH=CH or C≡C; R is H, an alkali metal, an amine salt, or an ⊁12C hydrocarbon or chlorhydrocarbon residue; m is 0 or 1; n is 0-6; p is 0-6; and Y and Z are O or H$_2$ except that Y and Z are not both O; have similar biological properties to the prostaglandins or are antagonists of prostaglandins.

French Patent Application No. 2258376 discloses that 10-aza prostaglandins of formula (II)":

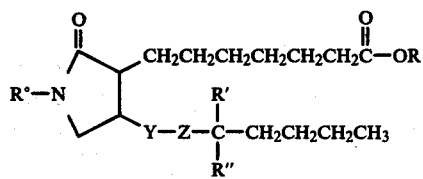

wherein R=H or lower alkyl; R' and R"=CH$_3$ or C$_2$H$_5$; R°=H or lower alkyl; Y=—CH$_2$CH$_2$—, or —CH=CH—; Z=—CO or —CH(~OH)—; are useful in the treatment of blood pressure and gastro-intestinal disorders, and in the preparation for confinement.

Belgian Patent No. 835989 discloses that compounds of the formula (III)":

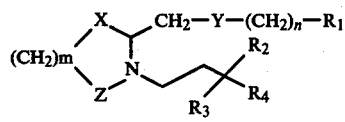

wherein:
X is CO, protected CO, CROH in which R is hydrogen or C$_{1-4}$ alkyl and in which the OH moiety may be protected; Y is CH$_2$CH$_2$ or CH=CH; Z is CO or CH$_2$; n is 1 to 8; m is 1, 2 or 3; R$_1$ is hydrogen, CH$_2$OH, CH$_2$OH in which the OH moiety is protected, CO$_2$W wherein W is hydrogen or CO$_2$W represents an ester group in which the ester moiety contains from 1 to 12 carbon atoms, or CONH$_2$; R$_2$ is hydrogen, C$_{1-4}$ alkyl, or taken together with R$_3$ and the carbon atom to which it is attached represents a carbonyl group; R$_3$ is hydrogen, hydroxy or protected hydroxy; R$_4$ is hydrogen or C$_{1-9}$ alkyl; and salts thereof; have useful pharmacological activity.

A novel class of compounds also having useful pharmacological activity has now been discovered, which compounds are structurally distinct from the prior art referred to above.

Accordingly the present invention provides a compound of the formula (I):

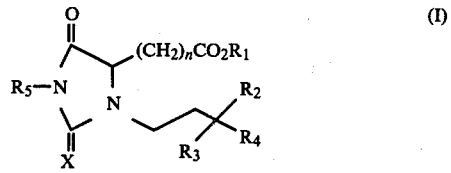

wherein:
X is O or S;
n is 1 to 8;
R$_1$ is hydrogen, or CO$_2$R$_1$ represents an ester group in which the R$_1$ moiety contains from 1-12 carbon atoms;
R$_2$ is hydrogen, C$_{1-4}$ alkyl, or phenyl;
R$_3$ is hydroxy or protected hydroxy;
R$_4$ is hydrogen, C$_{1-9}$ alkyl, C$_{3-8}$ cycloalkyl, C$_{3-8}$ cycloalkyl-C$_{1-6}$alkyl, phenyl, phenyl C$_{1-6}$alkyl, naphthyl, naphthyl-C$_{1-6}$-alkyl, any of which phenyl or naphthyl moieties may be substituted by one or more halogen, trifluoromethyl, C$_{1-6}$ alkyl, hydroxy, C$_{1-6}$ alkoxy, phenyl C$_{1-6}$ alkoxy or nitro groups; or
R$_2$ and R$_4$ taken with the carbon atom to which they are joined represent a C$_{5-8}$ cycloalkyl group;
R$_5$ is C$_{1-6}$ alkyl, C$_{1-6}$ alkyl substituted by a nitro, hydroxy, C$_{1-6}$ alkoxy, CO$_2$A, (CO$_2$A)$_2$, CN or halogen group, C$_{5-8}$ cycloalkyl, phenyl, phenyl-C$_{1-6}$ alkyl, phenyl-C$_{3-6}$ cycloalkyl, any of which phenyl moieties may be substituted by one or more halogen, trifluoromethyl, C$_{1-6}$ alkyl, C$_{1-6}$ alkoxy or nitro groups; or a group CO$_2$A; in R$_5$ when present A is hydrogen or CO$_2$A represents an ester group in which the A moiety contains from 1 to 12 carbon atoms; and salts thereof.

A group of compounds within formula (I) include those wherein:
X is O or S;
n is 4 to 8;
R$_1$ is hydrogen, or CO$_2$R$_1$ represents an ester group in which the R$_1$ moiety contains from 1 to 12 carbon atoms;
R$_2$ is hydrogen, C$_{1-4}$ alkyl, or phenyl;
R$_3$ is hydroxy or protected hydroxy;
R$_4$ is hydrogen, C$_{1-9}$ alkyl, C$_{5-8}$ cycloalkyl, C$_{5-8}$ cycloalkyl-C$_{1-6}$ alkyl, phenyl, phenyl C$_{1-6}$, alkyl, napthyl, napthyl-C$_{1-6}$-alkyl, any of which phenyl or naphthyl moieties may be substituted by one or more halogen, trifluoromethyl, C$_{1-6}$ alkyl, C$_{1-6}$ alkoxy or nitro groups;
R$_5$ is C$_{1-6}$ alkyl, phenyl, phenyl-C$_{1-6}$ alkyl, or a group CO$_2$A wherein A is hydrogen or CO$_2$A represents an ester group in which the A moiety contains from 1 to 12 carbon atoms; and salts thereof.

Particularly suitable compounds within formula (I) include those where X is O.

Suitably n is 5, 6 or 7, preferably 6.

R$_1$ is hydrogen or CO$_2$R$_1$ represents an ester group in which the R$_1$ moiety contains from 1 to 12 carbon atoms. Examples of $R_1$ include hydrogen, methyl, ethyl, n- and iso-propyl, n-, sec- and tert-butyl, phenyl, benzyl, toluyl and the like, while normally hydrogen or $C_{1-6}$ alkyl groups are preferred.

Suitable examples of $R_2$ include hydrogen, methyl, ethyl and phenyl. More suitably $R_2$ is hydrogen, methyl or ethyl, preferably methyl.

Suitable protected hydroxyl groups $R_3$ include readily hydrolysable groups such as acylated hydroxy groups in which the acyl moiety contains 1 to 4 carbon atoms, for example the acetoxy group; and hydroxy groups etherified by readily removable inert groups such as the benzyl group or like groups. Preferably $R_3$ is hydroxyl.

Suitable groups $R_4$ when $R_4$ is an alkyl group include $C_{4-9}$ alkyl groups. Such $C_{4-9}$ alkyl groups may be straight chain alkyl groups, such n-butyl, n-pentyl, n-hexyl and n-heptyl, or may be alkyl groups branched by one or two methyl groups (at the same or different carbon atoms). Thus for example, $R_4$ may be a group $CH_2R_7$, $CH(CH_3)R_7$ or $C(CH_3)_2R_7$, wherein $R_7$ is a straight chain alkyl group such that the carbon content of the resultant group $R_4$ is 4 to 9.

In general preferred groups $R_4$ when $R_4$ is an alkyl group include straight chain pentyl, hexyl and heptyl groups. Of these, straight chain hexyl is often the most useful. Other preferred groups $R_4$ include groups $CH(CH_3)R_7$ and $C(CH_3)_2R_7$ wherein $R_7$ is straight chain butyl, pentyl and hexyl.

Other suitable examples of $R_4$ when $R_4$ is an alkyl group include the lower alkyl groups, that is when $R_4$ is a $C_{1-4}$ alkyl group.

When $R_4$ is or contains a $C_{3-8}$ cycloalkyl moiety, the moiety may be cyclopropyl. The moiety may also be a $C_{5-8}$ cycloalkyl moiety such as a cyclohexyl moiety. Examples of suitable $C_{1-6}$ alkyl moieties when $R_4$ is a $C_{3-8}$ cycloalkyl-$C_{1-6}$ alkyl group include methyl, ethyl, propyl, butyl and amyl.

When $R_4$ is an aryl group as previously defined, suitable groups $R_4$ include phenyl, phenylmethyl, phenylethyl, phenyl n-propyl, phenyl n-butyl, naphthyl, naphthyl-methyl, naphthyl-ethyl, naphthyl n-propyl and naphthyl n-butyl, and such groups branched in the alkyl moiety by one or two methyl groups (at the same or different carbon atoms). These groups may be substituted in the phenyl or naphthyl moiety by normally one, two or three groups selected from those substituent groups listed hereinbefore. Examples of suitable substituent groups include fluorine, chlorine and bromine atoms and $CF_3$, methyl, ethyl, n- and iso-propyl, methoxy and ethoxy, n- and iso-propoxy and nitro groups. Other examples of such groups include hydroxy and benzyloxy. Preferably the aryl moieties when substituted by such groups will be mono or di-substituted.

Also, $R_2$ and $R_4$ taken with the carbon atom to which they are joined can represent a $C_{5-8}$ cycloalkyl group, such as the cyclohexyl group.

Suitable examples of $R_5$ include methyl, ethyl, n- and iso-propyl, n-, sec- and tert-butyl; phenyl; phenylmethyl, phenylethyl, phenyl-n-propyl, phenyl-n-butyl, and such phenylalkyl groups branched in their alkyl moities by one or two methyl groups (at the same or different carbon atoms). More suitably $R_5$ is $C_{1-6}$ alkyl such as methyl and ethyl.

$R_5$ may also be a phenyl-$C_{3-6}$ cycloalkyl group, in which case suitable examples of $R_5$ include phenylcyclopropyl.

When $R_5$ is or includes a phenyl moiety, it can optionally be substituted as described above for $R_4$ aryl groups.

When $R_5$ is $C_{5-8}$ cycloalkyl, it is suitably cyclohexyl.

When $R_5$ is, or contains, a group $CO_2A$, suitable examples of A include hydrogen, methyl, ethyl, n- and iso-propyl, n-, sec- and tert-butyl, phenyl, benzyl, toluyl and the like, while normally for A hydrogen or $C_{1-6}$ alkyl are preferred.

$R_5$ may also be a $C_{1-6}$ alkyl group substituted by a nitro, hydroxy, $C_{1-6}$ alkoxy (such as methoxy), $CO_2A$, $(CO_2A)_2$, CN or halogen group. In such cases often $R_5$ will be a methylene group substituted by one of these groups.

The compounds of the formula (I) may form conventional salts. Such salts include those with alkali and alkaline earth metals, suitably sodium and potassium, and ammonium and substituted ammonium salts.

From the aforesaid it will be seen that one particularly suitable group of compounds within formula (I) is of formula (II):

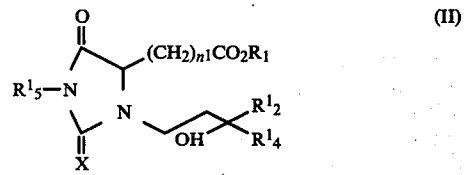

wherein:
X and $R_1$ are as defined in formula (I);
$n^1$ is 5, 6 or 7;
$R^1_2$ is hydrogen, methyl, ethyl or phenyl;
$R^1_4$ is hydrogen or $C_{1-9}$ alkyl;
$R^1_5$ is $C_{1-6}$ alkyl, phenyl, phenyl-$C_{1-6}$ alkyl, or a group $CO_2A$ wherein A is hydrogen or $CO_2A$ represents an ester group in which the A moiety contains from 1 to 12 carbon atoms; and salts thereof.

In formula (II) $n^1$ is preferably 6. Also suitably X is O.
$R^1_2$ is more suitably hydrogen, methyl or ethyl, preferably methyl.

While $R^1_4$ may be hydrogen or a $C_{1-9}$ alkyl group, it is normally a $C_{4-9}$ alkyl group. In such cases suitable and preferred straight chain and branched groups $R^1_4$ include those previously described as suitable and preferred for the groups $R_4$ when $R_4$ is a $C_{4-9}$ alkyl group. Such preferred groups $R^1_4$ include straight chain pentyl, hexyl and heptyl, and of these normally the most useful is straight chain hexyl. Other preferred groups $R^1_4$ include $CH(CH_3)R^1_7$ and $C(CH_3)_2R^1_7$ wherein $R^1_7$ is straight chain butyl, pentyl or hexyl.

Suitably $R^1_5$ is $C_{1-6}$ alkyl such as methyl and ethyl.

A second group of compounds within formula (I) of particular interest are those of formula (III):

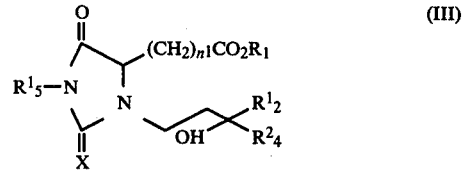

wherein:
X and $R_1$ are as defined in formula (I);
$n^1$ is 5, 6 or 7;
$R^1_2$ is hydrogen, methyl, ethyl or phenyl;
$R^2_4$ is a group of formula (IV):

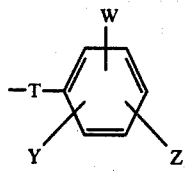

(IV)

wherein T is a bond, or a $C_{1-6}$ alkylene group which may be straight chain or branched by one or two methyl groups at the same or different carbon atoms; and W, Y and Z are each hydrogen or fluorine, chlorine or bromine atoms, or $CF_3$, methyl, ethyl, n- or iso-propyl, methoxy, ethoxy, n- or iso-propoxy or nitro groups;

$R^1_5$ is $C_{1-6}$ alkyl, phenyl, phenyl-$C_{1-6}$ alkyl, or a group $CO_2A$ wherein A is hydrogen or $CO_2A$ represents an ester group in which the A moiety contains from 1 to 12 carbon atoms; and salts thereof.

In formula (III) $n^1$ is preferably 6. Also suitably X is O.

$R^1_2$ is more suitably hydrogen, methyl or ethyl, preferably methyl.

In formula (IV) often T will be a group —$(CH_2)_q$— wherein q is 0 to 4. Also suitably W and Y are hydrogen.

Suitably $R^1_5$ is $C_{1-6}$ alkyl such as methyl and ethyl.

Another group of compounds within formula (I) of particular interest is of formula (V):

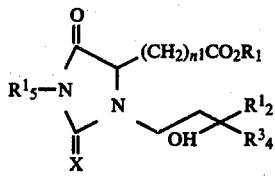

(V)

wherein:
X and $R_1$ are as defined in formula (I);
$n^1$ is 5, 6 or 7;
$R^1_2$ is hydrogen, methyl, ethyl or phenyl;
$R^3_4$ is a group of formula (VI):

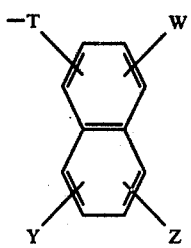

(VI)

wherein
T, W, Y and Z are as defined in formula (IV);
$R^1_5$ is $C_{1-6}$ alkyl, phenyl, phenyl-$C_{1-6}$ alkyl, or a group $CO_2A$ wherein A is hydrogen or $CO_2A$ represents an ester group in which the A moiety contains from 1 to 12 carbon atoms; and salts thereof.

In formula (V) $n^1$ is preferably 6. Also suitably X is O.
$R^1_2$ is more suitably hydrogen, methyl or ethyl, preferably methyl.

In formula (V) often T will be a group —$(CH_2)_q$— wherein q is 0 to 4. Also suitably W and Y are hydrogen.

Suitably $R^1_5$ is $C_{1-6}$ alkyl such as methyl and ethyl.

A further group of compounds within formula (I) of interest are of formula (VII):

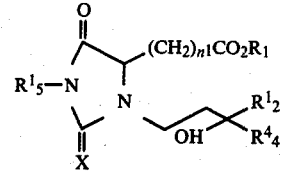

(VII)

wherein:
X and $R_1$ are as defined in formula (I);
$n^1$ is 5, 6 or 7;
$R^1_2$ is hydrogen, methyl, ethyl or phenyl;
$R^4_4$ is a group of formula (VIII):

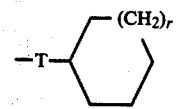

(VIII)

wherein
T is as defined in formula (IV) and
r is 0 to 3;
$R^1_5$ is $C_{1-6}$ alkyl, phenyl, phenyl-$C_{1-6}$ alkyl, or a group $CO_2A$ wherein A is hydrogen or $CO_2A$ represents an ester group in which the A moiety contains from 1 to 12 carbon atoms; and salts thereof.

In formula (VII) $n^1$ is preferably 6. Also suitably X is O.

$R^1_2$ is more suitably hydrogen, methyl, or ethyl, preferably methyl.

In formula (VIII) often T will be a group —$(CH_2)_q$— wherein q is 0 to 4. Also suitably r is 1.

Suitably $R^1_5$ is $C_{1-6}$ alkyl such as methyl and ethyl.

One compound of the invention that is particularly preferred for its useful activity is 1-(3'-hydroxy-3'-methyl-n-nonyl)-3-methyl-5-(6''-carboxy-n-hexyl)hydantoin.

The present invention further provides a process for the preparation of the compounds of the formula (I), which process comprises the cyclisation of a compound of formula (IX):

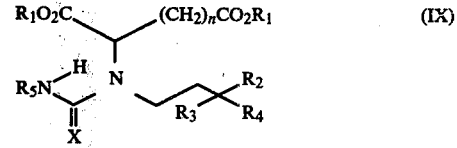

(IX)

wherein the variable groups are as defined; and thereafter if desired or necessary converting $R_1$ and/or $R_3$ in the thus formed compound into other variables $R_1$ and $R_3$.

Compounds of the formula (IX) are conveniently prepared in situ during the reaction of a compound of the formula:

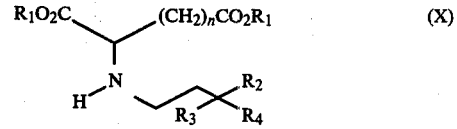

(X)

wherein n, $R_1$, $R_2$, $R_3$ and $R_4$ are as defined, with $R_5NCX$, a preferred process of the invention. This process is suitably carried out under reflux in an inert solvent such as benzene and the like. It should be stated that when in this reaction $R_5$ is a sterically hindered group then this reaction may proceed only as far as the uncyclised compound of formula (IX), in which case the necessary cyclisation of the compound (IX) can be achieved with a strong base, such as sodium hydride or sodium ethoxide, in a dry organic solvent. Sodium ethoxide in benzene, or potassium t-butoxide in toluene, benzene or hexamethyl phosphoramide are suitable reagents.

The conversion of a compound of the formula (I) to another compound of the formula (I) wherein $R_1$ and/or $R_3$ are altered when desired or necessary, may be achieved in conventional manner.

For example, if desired the group $R_1$ in the compound may be varied by conventional esterification and/or de-esterification reactions. Similarly protected $R_3$ hydroxy moieties may be deprotected in conventional manner. For example when $R_3$ is a benzyloxy group, the benzyl group may readily be removed by hydrogenolysis. Thus it may be seen that 'protected hydroxy' compounds of the formula (I) are useful intermediates in the preparation of the corresponding 'free hydroxy' compounds of the formula (I). Also when a compound of the formula (I) contains an acidic hydrogen atom, salts thereof may be prepared in conventional manner for example by reacting the compound of the formula (I) with the required base.

Also intermediates of the formula (I) which however are unsubstituted in the 3-position may be converted to the corresponding compounds of this invention wherein $R_5$ is as defined above by conventional substitution reactions with $R_5X$ wherein X is a displaceable group such as a halide or other good leaving group. In such reactions it may be necessary to first convert the unsubstituted compound to an alkali metal salt.

The skilled man will realise that in some such cases substitutions will also substitute a $R_1$ hydrogen. Thus if a compound is desired wherein $R_1$ is hydrogen, in such cases it will be preferred to esterify the $R_1$ hydrogen before the substitution reaction, and then de-esterify after the substitution reaction, to give the desired $R_1$ hydrogen compound.

Intermediates of formula (I) which are unsubstituted in the 3-position can be obtained through the reaction of a compound of formula (X) with an isocyanate or isothiocyanate.

When $R_1$ is hydrogen, this cyclisation may suitably be carried out by reacting a salt $M^+C^-NX$, wherein $M^+$ is a metal ion and X is O or S as defined, with a compound of formula (X). The metal salt of a compound of formula (IX) thus obtained can be converted to the acid of formula (IX) with mineral acid, and then the cyclisation completed in aqueous conditions at acid pH, for example in 25% aqueous acid. Suitably $M^+$ is a sodium or potassium ion, preferably a potassium ion.

When $R_1$ is other than hydrogen a compound of formula (X) is cyclised by reaction with $M^+C^-NX$. This conversion may suitably be achieved using a hydrochloride salt of the compound of the formula (X) and reacting that salt in aqueous solution at reflux, or in aqueous dichloromethane with a phase transfer catalyst.

It is believed that the compounds of formula (IX) are novel, and thus they form an important part of this invention as intermediates.

The compounds of the formula (X) may be prepared by the method disclosed in Belgian Pat. No. 835989, or by analogous methods thereto.

It will of course be realised that the compounds of the formula (I) have asymmetric centres, and thus are capable of existing in a number of stereoisomeric forms. The invention extends to each of these stereoisomeric forms, and to mixtures thereof. The different stereoisomeric forms may be separated one from the other by the usual methods.

Compounds within the formula (I) have useful pharmacological activity. For example compounds within the formula (I) have anti-gastric secretion activity e.g. anti-ulcer activity, cardiovascular activity e.g. anti-hypertensive activity, platelet aggregation inhibition activity, affect the respiratory tract e.g. bronchodilator activity, and have anti-fertility, smooth muscle and anti-arrythmic activity.

In general it may be said that compounds within the formula (I) have a range of pharmacological activities similar to those shown by the natural prostaglandins, but that these activities tend to be rather more selective.

The invention therefore also provides a pharmaceutical composition comprising a compound of the formula (I) and a pharmaceutically acceptable carrier.

Clearly the formulation of the said pharmaceutical composition will depend on the nature of the activity shown by the chosen compound of the formula (I), and on other factors such as a preference in a particular area of therapy for a particular mode of administration.

The compositions may be in the form of tablets, capsules, powders, granules, lozenges or liquid preparations, such as oral or sterile parenteral solutions of suspensions.

Tablets and capsules for oral administration may be in unit dose presentation form, and may contain conventional excipients such as binding agents, fillers, tabletting lubricants, disintegrants, and acceptable wetting agents and the like. The tablets may be coated according to methods well known in normal pharmaceutical practice. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, emulsifying agents, non-aqueous vehicles (which may include edible oils), preservatives, and if desired conventional flavouring or colouring agents, and the like.

For parenteral administration, fluid unit dosage forms are prepared utilizing the compound of the formula (I) and a sterile vehicle. The compound, depending on the vehicle and concentration used, can be either suspended or dissolved in the vehicle. In preparing solutions the compound can be dissolved for injection and filter sterilized before filling into a suitable vial or ampoule and sealing. Advantageously, adjuvants such as a local anaesthetic, preservatives and buffering agents can be dissolved in the vehicle. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

When appropriate, the compositions of this invention may be presented as an aerosol for oral administration, or as a microfine powder for insufflation.

As is common practice, the compositions will usually be accompanied by written or printed directions for use in the medical treatment concerned.

It will of course be realised that the precise dosage used in the treatment of any of the hereinbefore described disorders will depend on the actual compound of the formula (I) used, and also on other factors such as the seriousness of the disorder being treated.

The invention also provides a method of treatment and/or propylaxis of disorders in human beings or animals which comprises the administration to the sufferer of an effective amount of a compound of the formula (I).

Normally however the compounds will be used in the therapy of human disorders.

The following Examples illustrate the preparation of compounds of the formula (I) and their pharmacological properties.

EXAMPLE 1

Compound 1

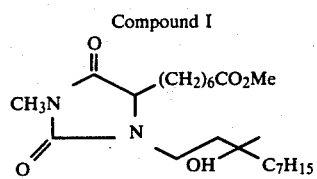

Dimethyl 2-[N-3'-hydroxy-3'-methyl-n-decyl]aminoazelate (9.6 g) was refluxed with methyl iso-cyanate (1.365 g) for 3 hours in dry benzene (80 mls). The benzene was evaporated in vacuo to give a pale yellow gum (10.2 g). This was chromatographed on kieselgel (packing ratio 30:1), using chloroform as eluant to give 1-(3'-hydroxy-3'-methyl-n-decyl)-3-methyl-5-(6''-methoxycarbonyl-n-hexyl)hydantoin as a clear oil (6 g).

The compounds shown in Table 1 were prepared in a similar manner.

Table I

| Compound number | $R_1$ | $R_2$ | $R_4$ | $R_5$ | n |
|---|---|---|---|---|---|
| 2 | $C_2H_5$ | $CH_3$ | $C_6H_{13}$ | $C_2H_5$ | 6 |
| 3 | $C_2H_5$ | $CH_3$ | $C_6H_{13}$ | $CH_3$ | 6 |
| 4 | $CH_3$ | | ⌬ | $CH_3$ | 6 |
| 5 | $CH_3$ | $CH_3$ | $(CH_2)_2Ph$ | $CH_3$ | 6 |
| 6 | $CH_3$ | $CH_3$ | $C_6H_{13}$ | $CH_3$ | 6 |
| 7 | $CH_3$ | $CH_3$ | $CH(CH_3)C_4H_9$ | $CH_3$ | 6 |
| 8 | $CH_3$ | $CH_3$ | Ph | $CH_3$ | 6 |
| 9 | $CH_3$ | $CH_3$ | $C_6H_{13}$ | Ph | 6 |
| 10 | $CH_3$ | $CH_3$ | $(CH_2)_2$-⌬-$CF_3$ | $CH_3$ | 6 |
| 11 | $CH_3$ | $CH_3$ | $CH_3$ | $CH_3$ | 6 |
| 12 | $CH_3$ | $CH_3$ | $C_6H_{13}$ | ⌬ | 6 |
| 35 | $CH_3$ | $CH_3$ | $C_6H_{13}$ | Ph-△ | 6 |
| 36 | $C_2H_5$ | $CH_3$ | $C_6H_{13}$ | $CH_3$ | 7 |
| 37 | $C_2H_5$ | $CH_3$ | $C_6H_{13}$ | $CH_3$ | 5 |
| 38 | $CH_3$ | $CH_3$ | $C_6H_{13}$ | $CH_3$ | 1 |

EXAMPLE 2

Compound 13

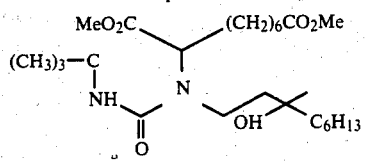

Dimethyl 2-[N-(3'-hydroxy-3'-methyl)-n-nonyl]aminoazelate (20 g) was refluxed with t-butyl isocyanate (5.12 g) in dry benzene (200 ml) for 3 hours. The benzene was evaporated in vacuo to give a pale yellow gum (20 g). The gum was chromatographed on kieselgel (600 g) using chlorogorm as eluant to give dimethyl 2-[N-(3'-hydroxy-3'-methyl-n-nonyl)-N-(N'-t-butylformamido)]aminoazelate (11.6 g) as a clear gum.

EXAMPLE 3

Compound 14

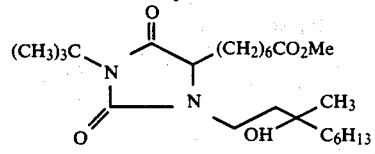

Dimethyl 2-[N-(3'-hydroxy-3'-methyl-n-nonyl)-N-(N'-t-butylformamido)]aminoazelate (10 g) was refluxed with potassium t-butoxide (2.5 g) in dry toluene (150 ml) for 3 hours. The toluene was evaporated in vacuo and the resulting gum was partitioned between ether and very dilute hydrochloric acid. The ether solution was washed with brine then dried (MgSO4) and evaporated in vacuo to give a yellow gum (8.4 g). The gum was chromatographed on kieselgel (250 g) using chloroform as eluant to give 1-(3'-hydroxy-3'-methyl-n-nonyl)-3-t-butyl-5-(6''-methoxycarbonyl-n-hexyl)-hydantoin (5.2) as a clear gum.

EXAMPLE 4

Compound 15

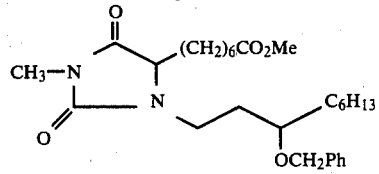

Dimethyl 2-[N-3'-benzyloxy-n-nonyl]aminoazelate (20 g) was refluxed with methyl iso-cyanate (2.46 g) in dry benzene (200 ml) for 3 hours. The benzene was evaporated in vacuo to give a deep yellow oil which was chromatographed on kieselgel (30:1 packing ratio), using chloroform as eluant, to give 1-(3'-benzyloxy-n-nonyl)3-methyl-5-(6''-methoxycarbonyl-n-hexyl)hydantoin (9 g) as a colourless gum.

EXAMPLE 5

Compound 16

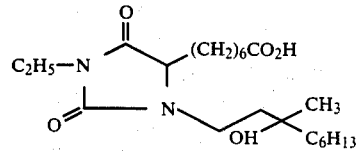

1-(3'-hydroxy-3'-methyl-n-nonyl)-3-ethyl-5-(6"-ethoxycarbonyl-n-hexyl)hydantoin (1.1 g) was refluxed overnight with 10% aqueous potassium carbonate solution (7.5 ml) and ethanol (30 ml). The solution was cooled and acidified with concentrated hydrochloric acid. The product was extracted into ether (3 × 100 ml). The ether solution was extracted with 5% sodium bicarbonate solution. The resulting aqueous phase was back-washed with ether then was acidified with dilute hydrochloric acid. The product was extracted into ether and the ether solution was washed with brine, dried (MgSO4) and evaporated in vacuo to give 1-(3'-hydroxy-3'-methyl-n-nonyl)-3-ethyl-5-(6"-carboxy-n-hexyl)hydantoin as a colourless gum (770 mg).

The compounds shown in Table 2 were prepared in a similar manner.

Table 2

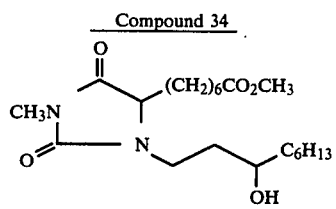

| Compound number | R2 | R4 | R5 | n |
|---|---|---|---|---|
| 17 | CH3 | C7H15 | CH3 | 6 |
| 18 | CH3 | C2H5 | CH3 | 6 |
| 19 | CH3 | ⬡ (cyclohexyl) | CH3 | 6 |
| 20 | CH3 | (CH2)2Ph | CH3 | 6 |
| 21 | CH3 | C6H13 | CH3 | 6 |
| 22 | CH3 | CH(CH3)C4H9 | CH3 | 6 |
| 23 | CH3 | Ph | CH3 | 6 |
| 24 | H | C6H13 | CH3 | 6 |
| 25 | CH3 | C6H13 | C(CH3)3 | 6 |
| 26 | CH3 | C6H13 | Ph | 6 |
| 27 | CH3 | (CH2)2-C6H4-CF3 | CH3 | 6 |
| 28 | CH3 | CH3 | CH3 | 6 |
| 29 | CH3 | C6H13 |  |  |
| 39 | CH3 | C6H13 | ⬡ (cyclohexyl) | 6 |
| | | | Ph-△ | |
| 40 | CH3 | C6H13 | CH3 | 7 |
| 41 | CH3 | C6H13 | CH3 | 5 |
| 42 | CH3 | C6H13 | CH3 | 1 |
| 48 | CH3 | C6H13 | CH2OCH3 | 6 |
| 49 | CH3 | C6H13 | CH2CO2H | 6 |

EXAMPLE 6

Compound 30

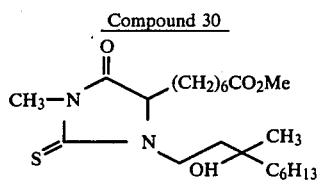

Dimethyl 2-[N-3'-hydroxy-3'-methyl-n-nonyl]aminoazelate (10 g) was refluxed with methyl iso-thiocyanate (1.89 g) in dry toluene (100 ml) for 3 hours. The toluene was evaporated in vacuo to give a yellow oil (11.1 g). The oil was chromatographed on kieselgel (330 g) using chloroform as eluant to give 1-(3'-hydroxy-3'-methyl-n-nonyl)-3-methyl-5-(6"-methoxycarbonyl-n-hexyl)-2-thiohydantoin (9.49 g) as a pale yellow oil.

The compounds shown in Table 3 were prepared in a similar manner:

Table 3

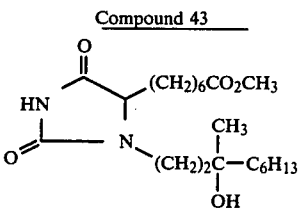

| Compound No. | R1 | R2 | R4 | R5 |
|---|---|---|---|---|
| 31 | C2H5 | CH3 | C6H13 | CH3 |
| 32 | CH3 | CH3 | CH3 | CH3 |

EXAMPLE 8

Compound 34

1-(3'-Benzyloxy-n-nonyl)-3-methyl-5-(6"-methoxycarbonyl-n-hexyl)hydantoin (5g) was hydrogenolysed over 10% palladium/charcoal, in dry dimethoxyethane (50 mls), at room temperature and atmospheric pressure. The reaction mixture was then filtered through kieselguhr and the dimethoxyethane was evaporated in vacuo to give a colourless oil (3.8g). The oil was chromatographed on silica gel (110g) using chloroform as eluant to give 1-(3'-hydroxy-n-nonyl)-3-methyl-5-(6"-methoxycarbonyl-n-hexyl)hydantoin as a colourless oil (2.48g).

EXAMPLE 9

Compound 43 (a)

Dry hydrogen chloride gas was passed into an ice-cold solution of dimethyl 2-[N-(3'-hydroxy-3'-methyl)-n-nonyl] aminoazelate (40 g) in dry ether (1 l). The ether was evaporated in vacuo and the resulting hydrochloride was stirred with water (300 ml). A solution of potassium cyanate (8.2 g; 1.01 eq) in water (20 ml) was added and the resulting suspension was stirred at room temperature for 1.5 hours then at reflux for 1.5 hours. The mixture was allowed to cool and the product was extracted into dichloromethane. The dichloromethane solution was washed with brine until the washings were neutral then was dried and evaporated to give a yellow gum (38 g). A sample was purified via column chromatography (silica gel; 30:1) using chloroform, and chloroform methanol mixtures as eluants to give 1-(3'- hydroxy-3'-methyl-n-nonyl)-5-(6''-methoxycarbonyl-n-hexyl) hydantoin as a pale yellow gum.

EXAMPLE 9

Compound 44

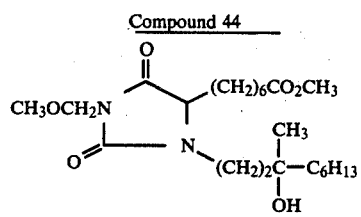

1-(3'-Hydroxy-3'-methyl-n-nonyl)-5-(6''-methoxycarbonyl-n-hexyl) hydantoin (5g) in dry dimethylformamide (10 ml) was added to a stirred suspension of sodium hydride (376 mg; 80% oil dispersion) in dry dimethylformamide (20 ml), under nitrogen, at room temperature. The mixture was stirred overnight. Chloromethyl methyl ether (1.01 g) in dry dimethylformamide (10 ml) was added dropwise and the mixture was stirred for 24 hours at room temperature. The product was partitioned between very dilute hydrochloric acid and ether. The ether solution was washed with 5% aqueous sodium hydroxide solution, and with brine until the washings were neutral, then was dried and evaporated in vacuo to give a yellow oil (4.1 g). The oil was chromatographed on silica gel (30:1) using chloroform, 1% methanol/chloroform and 2% methanol/chloroform as eluants to give 1-(3'-hydroxy-3'-methyl-n-nonyl)-3-methoxymethyl-5-(6''-methoxycarbonyl-n-hexyl) hydantoin (2.5 g) as a pale yellow gum.

The compounds prepared in Table 7 were prepared in a similar manner.

Table 7

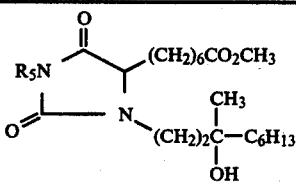

| Compound number | $R_5$ X | $R_5$ |
|---|---|---|
| 45 | $BrCH_2CO_2CH_3$ | $CH_2CO_2CH_3$ |
| 46 | $BrCH_2CN$ | $CH_2CN$ |
| 47* | $BrCH(CO_2CH_3)_2$ | $CH(CO_2CH_3)_2$ |
| 51 | $BrCH_2Ph$ | $CH_2Ph$ |

*The alkali extraction procedure was eliminated.

EXAMPLE 10

Compound 50

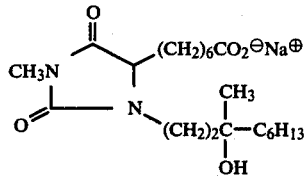

A 1% solution of sodium hydroxide in dry methanol (1 equivalent) was added to a solution of 1-(3'-hydroxy-3'-methyl-n-nonyl)-3-methyl-5-(6''-carboxy-n-hexyl) hydantoin in dry methanol at room temperature. The methanol was evaporated in vacuo at 30° C. and the product was triturated with 40/60 petroleum ether. The product was collected and dried over sodium hydroxide in a vacuum desiccator then was ground to a fine, pale yellow powder.

In similar manner was prepared the corresponding lithium salt.

Analytical Data

Compound 1

I.R. ($cm^{-1}$) : 3450, [OH]; 1760, 1700, [$-\overset{|}{N}-\overset{\|}{\underset{O}{C}}-\overset{|}{N}-\overset{\|}{\underset{O}{C}}-$];

1730, [$-CO_2CH_3$],

NMR, ($\tau$) : 7.15, (s), [OH];

7.05, (s), [$-\overset{|}{N}-CH_3$];

6.95 to 6.35, (m), [$-\overset{|}{N}-CH_2-$];
6.35, (s). [$-CO_2CH_3$];

6.0, (broad t), [$-\overset{|}{N}-CH$].

Analysis: $C_{23}H_{42}N_2O_5$
requires: C, 64.76; H, 9.92; N, 6.57%.
found: C, 64.44; H, 9.92; N, 6.71%.

Mass Spec: $C_{23}H_{42}N_2O_5$
requires: 426.3093
found: 426.3065

Compound 2

I.R. ($cm^{-1}$) : 3500, [OH]; 1700, 1760, [$-\overset{|}{N}-\overset{\|}{\underset{O}{C}}-\overset{|}{N}-\overset{\|}{\underset{O}{C}}-$];

1730, [$-CO_2Et$]

NMR ($\tau$) : 7.2, (s) [OH]; 6.2 to 6.8, (m),
($CCl_4$)

[$CH_3CH_2\overset{|}{N}-$; $-\overset{|}{N}-CH_2$];

5.9, (m) [$-\overset{|}{N}-CH;CO_2CH_2CH_3$]

Compound 3

I.R. ($cm^{-1}$) : 3500, [OH]; 1710, 1760[$-\overset{|}{N}-\overset{\|}{\underset{O}{C}}-\overset{|}{N}-\overset{\|}{\underset{O}{C}}-$];

1730, [$-CO_2Et$]

NMR ($\tau$) :

7.2, (s), [OH]; 7.0, (s), [$-\overset{|}{N}-CH_3$];

6.2 to 7, (m), [$-\overset{|}{N}-CH_2$];

5.9, (m) [$-\overset{|}{N}-CH; -CO_2CH_2CH_3$]

Compound 4

I.R. ($cm^{-1}$) : 3500, [OH]; 1700, 1760,

[$-\overset{|}{N}-\overset{\|}{\underset{O}{C}}-\overset{|}{N}-\overset{\|}{\underset{O}{C}}-$];

1720, [$-CO_2-CH_3$].

Compound 4

NMR (τ) :

7.05, (s), [—N(|)—CH₃; OH];

6.2 to 6.9, (m), [—N(|)—CH₂];
6.35, (s), [—CO₂CH₃]

6.0, (t), [—N(|)—CH]

Analysis: $C_{20}H_{34}N_2O_5$
requires: C, 62.80; H, 8.96; N, 7.32%
found: C, 62.61; H, 8.95; N, 7.19%

Mass Spec: $C_{20}H_{34}N_2O_5$
requires: 382.2468
found: 382.2466

Compound 5

I.R. (cm⁻¹) : 3500, [OH]; 1700, 1760, $$[-\overset{|}{N}-\underset{\overset{\|}{O}}{C}-\overset{|}{N}-\underset{\overset{\|}{O}}{C}-];$$

1730, [—CO₂CH₃].

NMR (τ) : 7.75, (t), [—CH₂CO₂CH₃];
7.3, (m), [—CH₂Ph];
7.1, (s), [—OH];

7.05, (s), [—N(|)—CH₃];

6.5 to 7.0, (m), [—N(|)—CH₂];
6.5, (s), [—CO₂CH₃];

6.05, (broad t), [—N(|)—CH].

Mass Spec: $C_{24}H_{34}N_2O_4$[m*—H₂O]
requires: 414.2518
found: 414.2523

Compound 6

I.R. (cm⁻¹) :

3500, [OH]; 1700, 1760, $[-\overset{|}{N}-\underset{\overset{\|}{O}}{C}-\overset{|}{N}-\underset{\overset{\|}{O}}{C}-]$;

1730, [—CO₂CH₃].

NMR (τ) : 7.3, (s), [OH];

7.05, (s), [—N(|)—CH₃];

6.3 to 7, (m), [—N(|)—CH₂];
6.35, (s), [—CO₂CH₃];

6.0, (m), [—N(|)—CH].

Analysis: $C_{22}H_{40}N_2O_5$
requires: C, 64.05; H, 9.77; N, 6.79%
found: C, 64.14; H, 9.68; N, 6.62%

Mass Spec: $C_{22}H_{38}N_2O_4$[m*—H₂O]
requires: 394.2832
found: 394.2848

Compound 7

I.R. (cm⁻¹) :

3500, [OH]; 1710, 1760, $[-\overset{|}{N}-\underset{\overset{\|}{O}}{C}-\overset{|}{N}-\underset{\overset{\|}{O}}{C}-]$;

1730, [—CO₂CH₃].

NMR (τ) : 7.75, (m), [—CH₂CO₂CH₃];
7.2, (s), [OH];

7.05, (s), [—N(|)—CH₃];

6.4 to 6.9, (m), [—N(|)—CH₂];
6.35, (s), [—CO₂CH₃];

6.05, (m), [—N(|)—CH].

Mass Spec: $C_{22}H_{38}N_2O_4$ [m*—H₂O]
requires: 394.2831
found: 394.2794

Compound 8

I.R. (cm⁻¹) : 3500, [OH]; 1700, 1760, $$[-\overset{|}{N}-\underset{\overset{\|}{O}}{C}-\overset{|}{N}-\underset{\overset{\|}{O}}{C}-];$$

1730, [—CO₂CH₃].

Compound 9

I.R. (cm⁻¹) : 3500 cm⁻¹, [OH]; 1710, 1770, $$[-\overset{|}{N}-\underset{\overset{\|}{O}}{C}-\overset{|}{N}-\underset{\overset{\|}{O}}{C}-];$$

1730, [—CO₂CH₃].

NMR (τ) : 7.75, (t), [—CH₂CO₂CH₃];
7.45, (s), [OH];

6.2 to 7.0, (m), [—N(|)—CH₂];
6.37, (s), [—CO₂CH₃];

5.95, (m), [—N(|)—CH];
2.65, (s), [C₆H₅].

Mass Spec: $C_{27}H_{42}N_2O_5$ requires: 474.3094
found: 474.3083

Compound 10

I.R. (cm⁻¹) :

3500, [OH]; 1710, 1760, $[-\overset{|}{N}-\underset{\overset{\|}{O}}{C}-\overset{|}{N}-\underset{\overset{\|}{O}}{C}-]$;

1730, [—CO₂CH₃].

NMR (τ) : 7.8, (t), [—CH₂CO₂CH₃];
7.3, (m), [—CH₂—Ar];

7.1, (s), [—N(|)—CH₃];

6.5 to 7, (m), [—N(|)—CH₂];
6.45, (s), [—CO₂CH₃];

6.1, (m), [—N(|)—CH];
2.65, (broad s), [—Ar].

Mass Spec: $C_{25}H_{33}N_2O_4F_3$[m*—H₂O]

requires: 482.2392
found: 482.2415

Compound 11

I.R. (cm$^{-1}$) : 3500, [OH]; 1710, 1760, 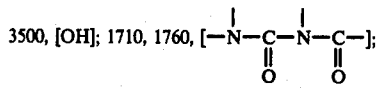;

1730, [—CO$_2$CH$_3$].

NMR (τ) : 7.75, (t), [—CH$_2$—CO$_2$CH$_3$];
7.15, (s), [OH];

7.1, (s), [—N(|)—CH$_3$];

6.2 to 7, (m), [—N(|)—CH$_2$];
6.4, (s), [—CO$_2$CH$_3$];
6.05, (m), [—N(|)—CH].

Mass Spec: C$_{17}$H$_{30}$N$_2$O$_5$
requires: 342.2154
found: 342.2144
Mass Spec: C$_{17}$H$_{28}$N$_2$O$_4$ [m* — H$_2$O]
requires: 324.2049
found: 324.2050

Compound 12

I.R. (cm$^{-1}$): 3500, [OH]; 1700, 1760, 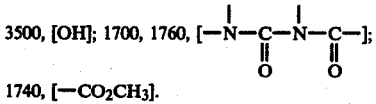;

1740, [—CO$_2$CH$_3$].

NMR (τ): 7.75, (t), [—CH$_2$CO$_2$CH$_3$];
7.1, (s), [OH];

6.2 to 7, (m), [—N(|)—CH$_2$];
6.4, (s), [—CO$_2$CH$_3$];

6.1, (m), [—N(|)—CH].

Mass Spec: C$_{27}$H$_{48}$N$_2$O$_5$
requires: 480.3564
found: 480.3536

Compound 13

I.R. (cm$^{-1}$): 3400, [OH]; 1740, [—CO$_2$CH$_3$];

1630, 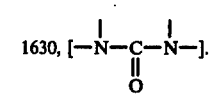.

Analysis: C$_{26}$H$_{50}$N$_2$O$_6$
requires: C, 64.16; H, 10.36; N, 5.76%
found: C, 64.22; H, 10.69; N, 5.43%

Mass Spec: C$_{25}$H$_{44}$N$_2$O$_4$ [m* — H$_2$O-CH$_3$OH]
requires: 436.3301
found: 436.3293

Compound 14

I.R. (cm$^{-1}$): 3500, [OH];

1700,1750, 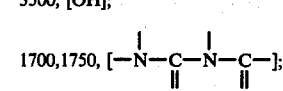;

1735, [—CO$_2$CH$_3$].

NMR (τ): 7.2, (s), [OH];

6.3 to 7,(m), [—N(|)—CH$_2$—];
6.3, (s), [—CO$_2$CH$_3$];

6.2, (m), [—N(|)—CH].

Analysis: C$_{25}$H$_{46}$N$_2$O$_5$
requires: C, 66.05; H, 10.20; N, 6.16%
found: C, 65.89; H, 10.30; N, 6.13%

Mass Spec: C$_{25}$H$_{46}$N$_2$O$_5$
requires: 454.3406
found: 454.3451
Mass Spec: C$_{25}$H$_{44}$N$_2$O$_4$ [m* — H$_2$O]
requires: 436.3301
found: 436.3317

Compound 15

I.R. (cm$^{-1}$):

1700, 1760, 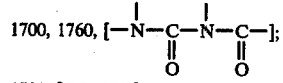;

1730, [CO$_2$CH$_3$].

NMR (τ):

7.1, (d), [—N(|)—CH$_3$];

6.3 to 7, (m), [—N(|)—CH$_2$];
6.35, (s), [—CO$_2$CH$_3$];

6.2 (m), [—N(|)—CH];
5.5, (s, with shoulder), [—OCH$_2$Ph];
2.75, (s), [—OCH$_2$Ph].

Analysis: C$_{28}$H$_{44}$N$_2$O$_5$
requires: C, 68.82; H, 9.08; N, 5.73%
found: C, 68.62; H, 9.21; N, 5.66%

Mass Spec: C$_{28}$H$_{44}$N$_2$O$_5$
requires: 488.3250
found: 488.3287

Compound 16

I.R. (cm$^{-1}$): 3700, to 2500, [—CO$_2$H; OH];

1760, 1710, 1700 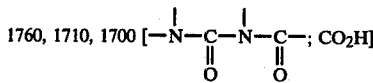

NMR (τ):

7.0 to 5.9, (m), [(—N(|)—CH$_2$)x2; —N(|)—CH];
4.4 (broad s), [—CO$_2$H; OH].

Mass Spec: C$_{22}$H$_{40}$N$_2$O$_5$
requires: 412.2937
found: 412.2917

Compound 17

I.R. (cm$^{-1}$): 3700 to 2400, [—CO$_2$H; OH];

1760, 1720, 1700, 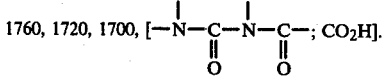.

19
-continued

Compound 17

NMR (τ):
7.05, (s), [—N(CH₃)—CH₃];

6.95 to 6.35, (m), [—N(—)—CH₂];

6, (broad s), [—N(—)—CH];
3.15, (broad s), [CO₂H; OH].

Analysis: $C_{22}H_{40}N_2O_5$
requires: C, 64.05; H, 9.77; N, 6.79%
found: C, 64.36; H, 9.99; N, 6.99%

Mass Spec: $C_{22}H_{38}N_2O_4$ [m*−H₂O]
requires: 394.2831
found: 394.2848

Compound 18

I.R. (cm⁻¹): 3700 to 2500, [CO₂H; OH];

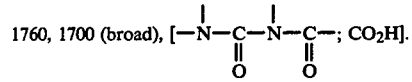
1760, 1700 (broad), [—N—C—N—C—; CO₂H].

NMR (τ):
(CD₃)₂CO
7.05, (s), [—N(—)—CH₃];

6.9 to 6.1, (m), [—N(—)—CH₂];

5.9 to 5.7, (s + t), [—N(—)—CH; CO₂H; OH].

Mass Spec: $C_{17}H_{30}N_2O_5$
requires: 342.2155
found: 342.2174

Compound 19

I.R. (cm⁻¹): 3700 to 2400, [CO₂H; OH]

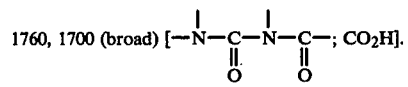
1760, 1700 (broad) [—N—C—N—C—; CO₂H].

NMR (τ):
7.1, (s), [N(—)—CH₃];

6.6, (m), [—N(—)—CH₂];
6.05, (broad s), [CO₂H; OH];

5.85, (t), [—N(—)—CH];

Analysis: $C_{19}H_{32}N_2O_5$
requires: C, 61.93; H, 8.75; N, 7.60%
found: C, 61.99; H, 8.97; N, 7.64%

Mass Spec: $C_{19}H_{32}N_2O_5$
requires: 368.2311
found: 368.2313

Compound 20

I.R. (cm⁻¹): 3700 to 2400, [CO₂H; OH];

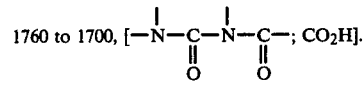
1760 to 1700, [—N—C—N—C—; CO₂H].

20
-continued

Compound 20

NMR (τ): 7.3, (m), [—CH₂Ph];

7.05, (s), [—N(—)—CH₃];

6.8 to 6.1, (m), [—N(—)—CH₂];
6.15, (s), [—CO₂H; OH];

5.8, (t), [—N(—)—CH].

Analysis: $C_{23}H_{34}N_2O_5$
requires: C, 66.01; H, 8.19; N, 6.69%
found: C, 65.82; H, 8.38; N, 6.37%

Mass Spec: $C_{23}H_{32}N_2O_4$ [m*-H₂O]
requires: 400.2362
found: 400.2323

Compound 21

I.R. (cm⁻¹): 3700 to 2400, [CO₂H; OH];

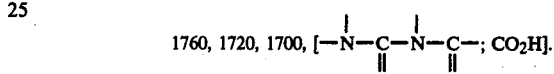
1760, 1720, 1700, [—N—C—N—C—; CO₂H].

NMR (τ):
7.1, (s), [—N(—)—CH₃];

6.8 to 6.1, (m), [—N(—)—CH₂];
6.1, (s), [CO₂H; OH];

5.85, (t), [—N(—)—CH].

Mass Spec: $C_{21}H_{36}N_2O_4$ [m*-H₂O]
requires: 380.2675
found: 380.2672

Compound 22

I.R. (cm⁻¹): 3700 to 2500, [CO₂H; OH];

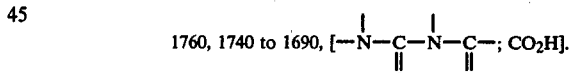
1760, 1740 to 1690, [—N—C—N—C—; CO₂H].

NMR (τ):
(CD₃)₂CO
7.1, (s), [—N(—)—CH₃];

6.9 to 6.1, (m), [—N(—)—CH₂];

5.9, (t), [—N(—)—CH];
5 to 3, (broad hump), [CO₂H; OH].

Analysis: $C_{21}H_{38}N_2O_5$
requires: C, 63.29; H, 9.61; N, 7.03%
found: C, 62.94; H, 9.79; N, 6.65%

Mass Spec: $C_{21}H_{36}N_2O_4$ [m*-H₂O]
requires: 380.2675
found: 380.2641

Compound 23

I.R. (cm⁻¹): 3700 to 2500, [CO₂H, OH];

Compound 23

I.R. (cm⁻¹): 1760, 1700 (broad), 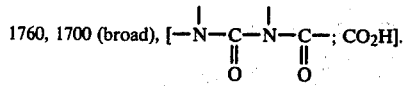; $CO_2H$.

NMR (τ):

7.25, (d), 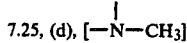;

6.9 to 6.1, (m), 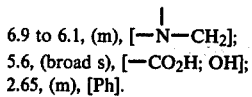;
5.6, (broad s), [—$CO_2H$; OH];
2.65, (m), [Ph].

Analysis: $C_{21}H_{30}N_2O_5$
requires: C, 64.60; H, 7.74; N, 7.17%
found: C, 64.83; H, 7.96; N, 6.91%

Mass Spec: $C_{21}H_{28}N_2O_4$ [m*-$H_2O$]
requires: 372.2049
found: 372.2037

Compound 24

I.R. (cm⁻¹): 3700 to 2500, [$CO_2H$; OH];

1760, 1710 (broad), 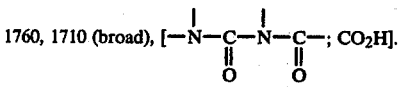; $CO_2H$.

NMR (τ):

7.1, (s), 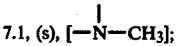;

6.8 to 6.1, (m), 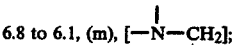;

5.9, (t), 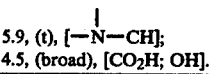;
4.5, (broad), [$CO_2H$; OH].

Analysis: $C_{20}H_{36}N_2O_5$
requires: C, 62.47; H, 9.44; N, 7.29%
found: C, 62.40; H, 9.59; N, 7.04%

Mass Spec: $C_{20}H_{36}N_2O_5$
requires: 384.2624
found: 384.2640

Compound 25

I.R. (cm⁻¹): 3700 to 2400, [$CO_2H$; OH];

1760, 1700 (broad) 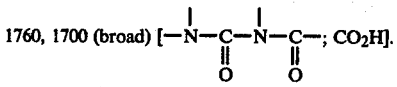; $CO_2H$.

NMR (τ): 6.7, (s), [$CO_2H$; OH];

7 to 6.3, (m), 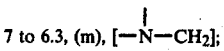;

6.1, (t), .

Analysis: $C_{24}H_{44}N_2O_5$
requires: C, 65.42; H, 10.07; N, 6.36%
found: C, 65.21; H, 10.29; N, 6.08%

Mass Spec: $C_{24}H_{44}N_2O_5$
requires: 440.3250
found: 440.3280

Compound 25

I.R. (cm⁻¹): 3200 to 2600, [$CO_2H$; OH];

1770, 1700 (broad), 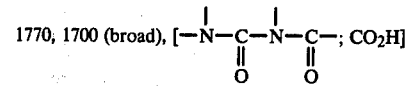; $CO_2H$]

NMR (τ):

7 to 6.1, (m), 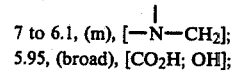;
5.95, (broad), [$CO_2H$; OH];

5.6, (t), 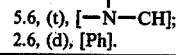;
2.6, (d), [Ph].

Mass Spec: $C_{26}H_{38}N_2O_4$ [m*-$H_2O$]
requires: 442.2832
found: 442.2841

Compound 27

I.R. (cm⁻¹): 3200 to 2400, [$CO_2H$; OH];

1770, 1730 to 1680, 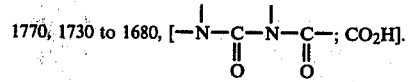; $CO_2H$.

NMR (τ): 7.8, (t), [—$CH_2$—$CO_2H$];
D₆DMSO 7.4, (m), [—$CH_2$—Ar];

7.15, (s), 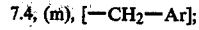;

7 to 6, (m), 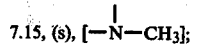;

5.8, (m), 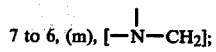.

Analysis: $C_{24}H_{33}N_2O_5F_3$
requires: C, 59.25; H, 6.83; N, 5.76%
found: C, 59.29; H, 7.13; N, 5.82%

Mass Spec: $C_{24}H_{31}N_2O_4F_3$ [m*-$H_2O$]
requires: 468.2236
found: 468.2245

Compound 28

I.R. (cm⁻¹): 3200 to 2400, [$CO_2H$; OH];

1760, 1730 to 1690, 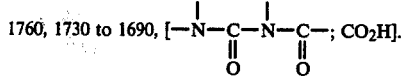; $CO_2H$.

NMR (τ): 7.75, (t), [—$CH_2$—$CO_2H$];
($D_6$DMSO)

7.1, (s), 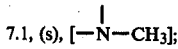;

7 to 6, (m), 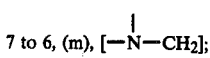;

5.8, (t), .

Analysis: $C_{16}H_{28}N_2O_5$
requires: C, 58.52; H, 8.59; N, 8.53%
found: C, 58.59; H, 8.71; N, 8.70%

Mass Spec: $C_{16}H_{28}N_2O_5$
requires: 328.1998
found: 328.1995

| Compound 29 | |
|---|---|
| I.R. (cm⁻¹): | 3200 to 2400, [CO₂H; OH]; 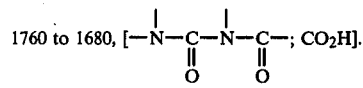 1760 to 1680, [—N—C—N—C—; CO₂H]. |
| NMR (τ): (CD₃)₂CO | 7 to 6.2, (m), [—N—CH₂]; 6.1, (broad s), [CO₂H; OH]; 6.0, (m), [—N—CH—C—]; 5.5, (m), [—C—N—CH]. |

Analysis: C₂₆H₄₆N₂O₅
requires: C, 66.92; H, 9.94; N, 6.00%
found: C, 66.57; H, 10.06; N, 6.25%

Mass Spec: C₂₆H₄₆N₂O₅
requires: 466.3406
found: 466.3403

| Compound 30 | |
|---|---|
| I.R. (cm⁻¹): | 3510, [OH]; 1750 to 1720, 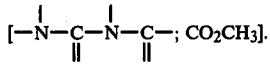 [—N—C—N—C—; CO₂CH₃]. |
| NMR (τ): | 7.75, (m), [OH; CH₂—CO₂CH₃]; 6.8, (s), [—N—CH₃]; 7 to 6.2, (m), [—N—CH₂]; 6.35, (s), [—CO₂CH₃]; 5.9, (m), [—N—CH]. |

Analysis: C₂₂H₄₀N₂O₄S
requires: C, 61.64; H, 9.41; N, 6.53; S, 7.48%
found: C, 61.71; H, 9.51; N, 6.54; S, 7.34%

Mass Spec: C₂₂H₃₈N₂O₃S [m*-H₂O]
requires: 410.2603
found: 410.2610

| Compound 31 | |
|---|---|
| I.R. (cm⁻¹): | 3500, [OH]; 1740, 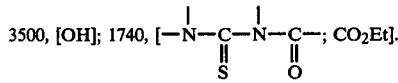 [—N—C—N—C—; CO₂Et]. |
| NMR (τ): | 7.7, (s), [OH]; 6.8, (s), 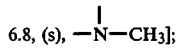 —N—CH₃; 6.9 to 6.2, (m), 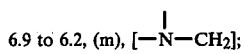 [—N—CH₂]; 5.9, (m),  [—N—CH; —CO₂CH₂CH₃]. |

Analysis: C₂₃H₄₂N₂O₄S
requires: C, 62.41; H, 9.56; N, 6.33; S, 7.24%
found: C, 62.54; H, 9.85; N, 6.05; S, 7.35%

Mass Spec: C₂₃H₄₂N₂O₄S
requires: 442.2865
found: 442.2866

| Compound 32 | |
|---|---|
| I.R. (cm⁻¹) | : 3500, [OH]; 1740, 1720, 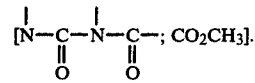 [N—C—N—C—; CO₂CH₃]. |
| NMR (τ) | : 7.45, (s), [OH]; 6.8, (s), 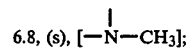 [—N—CH₃]; 6.9 to 6.2, (m), [—N—CH₂]; 6.4, (s), [—CO₂CH₃]; 5.9, (m), 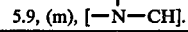 [—N—CH]. |

Mass Spec: C₁₇H₃₀N₂O₄S
requires: 358.1926
found: 358.1956

| Compound 34 | |
|---|---|
| I.R. (cm⁻¹) | : 3500, [OH]; 1760, 1710, 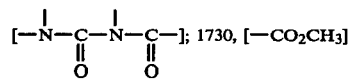 [—N—C—N—C—]; 1730, [—CO₂CH₃] |
| NMR (τ) | : 7.05, (s), 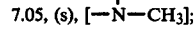 [—N—CH₃]; 6.7 to 6.2, (m), [—N—CH₂]; 6.35, (s), [—CO₂CH₃]; 6.0, (s), 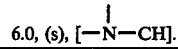 [—N—CH]. |

Analysis: C₂₁H₃₈N₂O₅
requires: C, 63.29; H, 9.61; N, 7.03%
found: C, 63.61; H, 9.83; N, 7.34%

Mass Spec: C₂₁H₃₈N₂O₅
requires: 398.2780
found: 398.2769

| Compound 35 | |
|---|---|
| I.R. (cm⁻¹) | : 3550, [OH]; 1770, 1730 (broad) 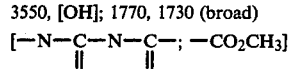 [—N—C—N—C—; —CO₂CH₃] |
| NMR (τ) | : 7.75 (t), [CH₂CO₂CH₃]; 7.35, (m), [Ph-CH]; 7.35, (s), [OH]; 7.0 to 6.2, (m), 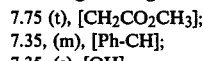 [—N—CH₂]; 6.4, (s), [—CO₂CH₃]; 6.1, (m), 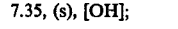 [—N—CH] × 2; 2.7, (s),  [Ph]. |

Mass Spec: C₃₀H₄₄N₂O₄ (m*-H₂O)
requires: 496.3301
found: 496.3303

Compound 36

I.R. (cm$^{-1}$) : 3550, [OH]; 1770, 1710 [$-\text{N}-\overset{\text{O}}{\underset{\|}{\text{C}}}-\text{N}-\overset{\text{O}}{\underset{\|}{\text{C}}}-$];

1730, [$-CO_2C_2H_5$].

NMR ($\tau$) : 7.7, (t), [$CH_2CO_2C_2H_5$];
7.5, (s), [OH];

7.0, (s), [$-\overset{|}{\text{N}}-CH_3$];

7.0 to 7.2, (m), [$-\overset{|}{\text{N}}-CH_2$];

6.05 (t), [$-\overset{|}{\text{N}}-CH$];

5.85, (q), [$-\overset{\text{O}}{\underset{\|}{\text{C}}}-O-CH_2CH_3$].

Mass Spec: $C_{24}H_{42}N_2O_4$ (m*-$H_2O$)
requires: 422.3144
found: 422.3156

Compound 37

I.R. (cm$^{-1}$) :

3500, [OH]; 1760, 1710, [$-\overset{|}{\text{N}}-\overset{\text{O}}{\underset{\|}{\text{C}}}-\overset{|}{\text{N}}-\overset{\text{O}}{\underset{\|}{\text{C}}}-$];

1720, [$-CO_2C_2H_5$].

NMR ($\tau$) : 7.75, (t), [$CH_2CO_2C_2H_5$];
7.5, (s), [OH];

7.05, (s), [$-\overset{|}{\text{N}}-CH_3$];

6.9 to 6.2, (m), [$-\overset{|}{\text{N}}-CH_2$];

6.05, (m), [$-\overset{|}{\text{N}}-CH$];
5.9, (q), [$-CO_2CH_2CH_3$].

Mass Spec: $C_{22}H_{38}N_2O_4$ (m*-$H_2O$)
requires: 394.2832
found: 394.2826

Compound 38

I.R. (cm$^{-1}$) :

3500, [OH]; 1770, 1710, [$-\overset{|}{\text{N}}-\overset{\text{O}}{\underset{\|}{\text{C}}}-\overset{|}{\text{N}}-\overset{\text{O}}{\underset{\|}{\text{C}}}-$];

1740, [$-CO_2CH_3$].

NMR ($\tau$) : 7.75, (s), [OH];
7.1, (m), [$CH_2CO_2CH_3$];

6.9 to 6.3 approx, (m), [$-\overset{|}{\text{N}}-CH_2$];

6.95, (s), [$-\overset{|}{\text{N}}-CH_3$];
6.25, (s), [$-CO_2CH_3$];

5.7, (t), [$-\overset{|}{\text{N}}-CH$].

Mass Spec: $C_{17}H_{28}N_2O_4$ (m*-$H_2O$)
requires: 324.2048
found: 324.2056

Compound 39

I.R. (cm$^{-1}$) : 3700 to 2500, [$-CO_2H$; OH];

1760, 1720 (broad), [$-\overset{|}{\text{N}}-\overset{\text{O}}{\underset{\|}{\text{C}}}-\overset{|}{\text{N}}-\overset{\text{O}}{\underset{\|}{\text{C}}}-$; $CO_2H$].

NMR ($\tau$) : 7.7, (m), [$CH_2CO_2H$];
7.3 m), (Ph-CH);

7.0 to 6.1, (m), [$-\overset{|}{\text{N}}-CH_2$];

5.9, (t), [$-\overset{|}{\text{N}}-CH$] $\times$ 2;
5.7, (broad s), [$CO_2H$; OH];
2.75, (s), [Ph].

Mass Spec: $C_{29}H_{42}N_2O_4$ (m*-$H_2O$)
requires: 482.3145
found: 482.3184

Analysis: $C_{29}H_{44}N_2O_5$
requires: C, 69.57; H, 8.86; N, 5.60%.
found: C, 69.83; H, 9.05; N, 5.32%.

Compound 40

I.R. (cm$^{-1}$) : 3800 to 2500, [$-CO_2H$; OH];

1770, 1720 (broad), [$-\overset{|}{\text{N}}-\overset{\text{O}}{\underset{\|}{\text{C}}}-\overset{|}{\text{N}}-\overset{\text{O}}{\underset{\|}{\text{C}}}-$; $CO_2H$].

NMR ($\tau$) : 7.7, (t), [$CH_2CO_2H$];

7.1, (s), [$-\overset{|}{\text{N}}-CH_3$];

7.0 to 6.1, (m), [$-\overset{|}{\text{N}}-CH_2$];
6.2, (broad s), [$-CO_2H$; OH];

5,8, (t), [$-\overset{|}{\text{N}}-CH$].

Mass Spec: $C_{22}H_{38}N_2O_4$ (m*-$H_2O$)
requires: 394.2831
found: 394.2823

Analysis: $C_{22}H_{40}N_2O_5$
requires: C, 64.05; H, 9.77; N, 6.79%.
found: C, 63.98; H, 9.97; N, 6.57%.

Compound 41

I.R. (cm$^{-1}$) : 3700 to 2500, [$-CO_2H$; OH];

1760, 1710 (broad), [$-\overset{|}{\text{N}}-\overset{\text{O}}{\underset{\|}{\text{C}}}-\overset{|}{\text{N}}-\overset{\text{O}}{\underset{\|}{\text{C}}}-$; $-CO_2H$].

NMR ($\tau$) : 7.8, (t), [$CH_2CO_2H$];

7.2, (s), [$-\overset{|}{\text{N}}-CH_3$];

6.9 to 6.1, (m), [$-\overset{|}{\text{N}}-CH_2$];

5.95, (t), [$-\overset{|}{\text{N}}-CH$];
4.6 to 3.3, (hump), [$-CO_2H$; OH].

Mass Spec: $C_{20}H_{34}N_2O_4$ (m*-$H_2O$)
requires: 366.2518
found: 366.2513

Compound 42

Mass Spec: $C_{16}H_{26}N_2O_4$ (m*-$H_2O$)
requires: 310.1892
found: 310.1891

Compound 43

I.R. (cm$^{-1}$) : 3500, [OH]; 3300, [NH];

1770, 1710, $[-\underset{|}{N}-\underset{\|}{C}-\underset{|}{N}-\underset{\|}{C}-]$;
$\qquad\qquad\quad\; O\quad\;\; O$

1730, [—$CO_2CH_3$].

NMR (τ) : 7.85, (m), [$CH_2CO_2CH_3$];

7.5 to 6.5, (m), $[-\underset{|}{N}-CH_2]$;
6.4, (s), [—$CO_2CH_3$];

5.95, (broad s), $[-\underset{|}{N}-CH]$.

Mass Spec: $C_{21}H_{36}N_2O_4$ (m*-$H_2O$)
requires: 380.2675
found: 380.2659

Compound 44

I.R. (cm$^{-1}$) : 3500, [OH]; 1770, 1720 (broad), $[-\underset{|}{N}-\underset{\|}{C}-\underset{|}{N}-\underset{\|}{C}-; CO_2CH_3]$.
$\qquad\;\; O\quad\;\; O$ NMR (τ) : 7.8, (t), [—$CH_2CO_2CH_3$];
7.3, (s), [OH];

7 to 6, (m), $[-\underset{|}{N}-CH_2]$;
6.6, (s), (—$OCH_3$);
6.3, (s), [—$CO_2CH_3$];

5.9, (t), $[-\underset{|}{N}-CH]$;
5.2, (s), [$CH_2OCH_3$].

Mass Spec: $C_{23}H_{40}N_2O_5$ (m*-$H_2O$)
requires: 424.2937
found: 424.2942.

Compound 45

I.R. (cm$^{-1}$) : 3550, [OH]; 1760 to 1710, (broad), $[-\underset{|}{N}-\underset{\|}{C}-\underset{|}{N}-\underset{\|}{C}-; -CO_2CH_3]$.
$\qquad\;\; O\quad\;\; O$ NMR (τ) : 7.75, (t), [$CH_2CO_2CH_3$];
7.4, (s), [OH];

7 to 6.4, (m), $[-\underset{|}{N}-CH_2]$;
6.4, (s), [$CO_2CH_3$];
6.25, (s), [$CO_2CH_3$];

5.9, (s + m), $[-\underset{|}{N}-CH_2CO_2CH_3; -\underset{|}{N}-CH]$.

Mass Spec: $C_{24}H_{40}N_2O_6$ (m*-$H_2O$)
requires: 452.2886
found: 452.2892

Compound 46

I.R. (cm$^{-1}$) : 3500, [OH]; 1765, 1720 (broad), $[-\underset{|}{N}-\underset{\|}{C}-\underset{|}{N}-\underset{\|}{C}-; CO_2CH_3]$.
$\qquad\;\; O\quad\;\; O$ NMR (τ) : 7.7, (t), [—$CH_2CO_2CH_3$];
7.3, (s), [OH];

7.0 to 6.3, (m), $[-\underset{|}{N}-CH_2]$;
6.35, (s), [$CO_2CH_3$];

5.85, (m), $[-\underset{|}{N}-CH]$;
5.65, (s), [—$CH_2CN$].

Mass Spec: $C_{23}H_{37}N_3O_4$ (m*-$H_2O$)
requires: 419.2784
found: 419.2771

Analysis: $C_{23}H_{39}N_3O_5$
requires: C, 63.13; H, 8.98; N, 9.60%.
found: C, 63.21; H, 9.13; N, 9.31%.

Compound 47

I.R. (cm$^{-1}$) : 3500, [OH]; 1730, (very broad), $[-\underset{|}{N}-\underset{\|}{C}-\underset{|}{N}-\underset{\|}{C}-; CO_2CH_3]$.
$\qquad\;\; O\quad\;\; O$ NMR (τ) : 7.75 (t), [$CH_2CO_2CH_3$];
7.6, (s), [OH];

7 to 6.4 approx, (m), $[-\underset{|}{N}-CH_2]$;
6.4, (s), [—$CO_2CH_3$];

6.2, (s), [HC$\underset{CO_2CH_3}{\overset{CO_2CH_3}{<}}$];

5.9, (m), $[-\underset{|}{N}-CH]$;

4.9, (s), [HC$\underset{CO_2CH_3}{\overset{CO_2CH_3}{<}}$].

Mass Spec: $C_{26}H_{42}N_2O_8$ (m*-$H_2O$)
requires: 510.2941
found: 510.2937

Compound 48

I.R. (cm$^{-1}$) : 3200 to 2600, [—$CO_2H$; OH];

1770, 1700 (broad), $[-\underset{|}{N}-\underset{\|}{C}-\underset{|}{N}-\underset{\|}{C}-; CO_2H]$.
$\qquad\qquad\qquad\qquad\;\; O\quad\;\; O$ NMR (τ) : 7.7, (t), [—$CH_2CO_2H$];

7 to 6.1 approx, (m), $[-\underset{|}{N}-CH_2]$;
6.65, (s), [—$OCH_3$];

5.95, (m), $[-\underset{|}{N}-CH]$;

5.15, (s), $[-\underset{|}{N}-CH_2OCH_3]$;
4.3, (broad s), [$CO_2H$; OH].

Mass Spec: $C_{21}H_{34}N_2O_4$(m*-$H_2O$-MeOH)

requires: 378.2519
found: 378.2507

Compound 49

I.R. (cm$^{-1}$): 3600 to 2400, [CO$_2$H; OH];

1760 to 1690, 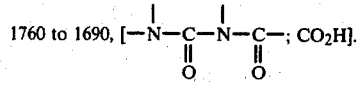 ; CO$_2$H].

Compound 50

Analysis: C$_{21}$H$_{37}$N$_2$O$_5$Na
requires: C, 59.98; H, 8.87; N, 6.66; Na, 5.47%.
found: C, 60.15; H, 9.19; N, 6.71; Na, 5.52%.

Compound 51

I.R. (cm$^{-1}$):

3500, [OH]; 1760, 1710, 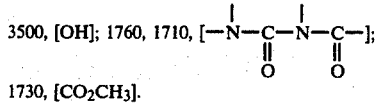;

1730, [CO$_2$CH$_3$].

NMR (γ): 7.8, (t), [—CH$_2$CO$_2$CH$_3$];
7.2, (hump), [—OH];
7 to 6.2 approx, (m), [—N—CH$_2$—];
6.4, (s), [—CO$_2$CH$_3$];
6.05, (t), [—N—CH];
5.45, (s), [CH$_2$Ph];
2.7, (broad s), [CH$_2$Ph].

PHARMACOLOGICAL DATA

Bronchodilation activity

1. The compounds were examined for their ability to inhibit 5-hydroxytryptamine or histamine induced bronchoconstriction in the anaesthetised, artificially respired guinea pig (Konzett-Rossler preparation). The compounds were administered intravenously. The results are shown in Table A.
2. The compounds were also examined for their ability to protect conscious guinea pigs against bronchoconstriction induced by an histamine aerosol (Herxheimer test). In these experiments the compounds were administered by aerosol or by oral administration. The results are shown in Table B. The results are the mean of several experiments.

| Compound number | ID$_{50}$ against 5-hydroxytryptamine-induced constriction μg/kg, i.v. |
|---|---|
| 1 | 4.5 |
| 2 | 6.8 |
| 3 | 0.4 |
| 4 | 220 |
| 6 | 1.5 |
| 7 | 3.3 |
| 16 | 5.8 |
| 17 | 8.5 |
| 19 | >220 |
| 21 | 0.6 |
| 22 | 3.2 |
| 23 | 60 |
| 24 | 6.0 |
| 27 | 30 |
| 31 | 4.2 |

Similar results were obtained against histamine-induced bronchoconstriction; for example, compound 21 also had an ID$_{50}$ of 0.6 μg/kg, i.v., against histamine-induced constriction.

TABLE B

| Compound number | Aerosol route Activity; μg/ml | Oral route Activity; mg/kg |
|---|---|---|
| 1 | A ; 10 | — |
| 2 | A ; 10 | — |
| 3 | A ; 1.0 | A ; 0.25 |
| 16 | A ; 10 | — |
| 17 | A ; 10 | — |
| 21 | A ; 0.25 | A ; 0.25 |

A = active

Anti-ulcer activity

Method

Anti-ulcer activity was assessed by the inhibition of indomethacin induced gastric damage in the rat according to the method of Eleghe (1974) Israeli J. Med. Sci. 10. 1451. Rats were starved overnight given 15 mg/kg indomethacin subcutaneously and sacrificed 4 hours later. Stomachs were reflated with n.saline, cut along the greater curvature pinned out and scored for gastric damage by the following system:

Score 1-3—according to degree of erythema and slight haemorrhage.
Score 4-6—according to degree of mucosal erosion.
Score 7-9—according to depth of gastric damage.

Groups of 7 rats were used for each treatment and the test compound or vehicle were administered 30 minutes prior to giving the indomethacin. Dose of test compound was 100 mg/kg orally and control groups receiving vehicle only were set up simultaneously. Mean values for each treatment were obtained using the above scoring system and the Mann Witney test applied for significance of difference between the values obtained with the treatments.

The results are shown in Table C.

TABLE C

| Compound number | Vehicle Control Mean Score + S.E. of Mean | Test Mean Score + S.E. of Mean |
|---|---|---|
| 17 | 4.86 ± 0.77 | 0.43 ± 0.30 (P<0.01) |
| 22 | 2.29 ± 0.87 | 0.00 ± 0.00 (P<0.05) |
| 25 | 3.86 ± 0.74 | 1.14 ± 0.74 (P<0.05) |
| 30 | 2.86 ± 0.83 | 0.14 ± 0.14 (P<0.05) |
| 31 | 2.00 ± 0.79 | 0.00 ± 0.00 |

Compared with vehicle only treatment, the compounds reduced the mean ulcer score and therefore have significant anti-ulcer activity.

Anti-secretory activity

The compounds were examined for their ability to inhibit pentagastrin-stimulated gastric acid secretion in the anaesthetised, perfused rat stomach preparation (Ghosh and Schild preparation). The compounds were administered intra-venously.

Compound 17 inhibited gastric acid secretion over the dose range 5-10 mg/kg, i.v.

Anti-platelet aggregation activity

The compounds were examined for their ability to inhibit platelet aggregation induced in vitro by collagen in human platelet rich plasma.

Compounds 18 and 17 inhibited aggregation by 100% and 34%, respectively, at a concentration of 100 μM.

The IC$_{50}$ for Compound 18 against collagen-induced aggregation was 7 μM.

Anti-arrythmic activity

The compounds were examined for anti-arrythmic activity by determining their ability to prevent heart fibrillation in mice exposed to chloroform.

Compound 17, when given intraperitoneally at 100 mg/kg, prevented fibrillation induced by chloroform in a group of 3 mice.

Toxicity

The compounds do not appear to be actualy toxic. For example, Compound 17 was not toxic in mice at doses up to 300 mg/kg, orally, or at doses up to 100 mg/kg, intraperitoneally, whereas Compound 21 was not toxic at doses up to 900 mg/kg, orally, in mice.

We claim:

1. A compound of the formula:

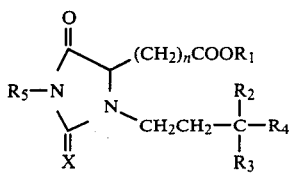

or a pharmaceutically acceptable salt thereof, wherein X is O or S;
  n has a value of from 1 to 8;
  $R_1$ is hydrogen; alkyl; phenyl or aralkyl of up to 12 carbon atoms;
  $R_2$ when taken alone is hydrogen; alkyl of 1 to 4 carbon atoms; or phenyl;
  $R_3$ is hydroxy, alkanoyloxy of 1 to 4 carbon atoms or benzyloxy;
  $R_4$ when taken alone is hydrogen; alkyl of 1 to 9 carbon atoms; cycloalkyl of 3 to 8 carbon atoms; phenyl; naphthyl; or alkyl of 1 to 6 carbon atoms substituted with phenyl, naphthyl or cycloalkyl of 3 to 8 carbon atoms; any of said phenyl rings and said naphthyl rings being unsubstituted or substituted with halo, trifluoromethyl, alkyl of 1 to 6 carbon atoms, hydroxy, alkoxy of 1 to 6 carbon atoms, phenylalkoxy wherein alkoxy contains from 1 to 6 carbon atoms or nitro;
  $R_2$ and $R_4$ taken together, together with the carbon atom to which they are joined, are cycloalkylidene of 5 to 8 carbon atoms;
  $R_5$ is alkyl of 1 to 6 carbon atoms unsubstituted or substituted with nitro, hydroxy, alkoxy of 1 to 6 carbon atoms, cyano, halo, carboxy or carbalkoxy wherein alkoxy contains up to 12 carbon atoms, cycloalkyl of 5 to 8 carbon atoms; phenyl; phenylalkyl wherein alkyl contains from 1 to 6 carbon atoms; phenylcycloalkyl wherein cycloalkyl contains 3 to 6 carbon atoms; carboxy or carbalkoxy wherein alkoxy contains up to 12 carbon atoms; any of said phenyl rings being unsubstituted or substituted with halo, trifluoromethyl, alkyl of 1 to 6 carbon atoms, alkoxy of 1 to 6 carbon atoms or nitro.

2. A compound according to claim 1 wherein X is O.

3. A compound according to claim 1 wherein n is 5, 6 or 7.

4. A compound according to claim 1 wherein $R_1$ is hydrogen or alkyl of 1 to 6 carbon atoms.

5. A compound according to claim 1 wherein $R_2$ is hydrogen or methyl.

6. A compound according to claim 1 wherein $R_3$ is hydroxy.

7. A compound according to claim 1 wherein $R_4$ is alkyl of 1 to 9 carbon atoms.

8. A compound according to claim 1 wherein $R_5$ is alkyl of 1 to 6 carbon atoms.

9. A compound according to claim 1 wherein $R_5$ is alkyl of 1 to 6 carbon atoms monosubstituted with a member of the group consisting of nitro, hydroxy, alkoxy of 1 to 6 carbon atoms, carboxy, carbalkoxy wherein alkoxy contains 1 to 6 carbon atoms cyano and halo or disubstituted with $(CO_2A)_2$ wherein A is hydrogen or alkyl of 1 to 6 carbon atoms.

10. A compound according to claim 9 wherein $R_5$ is nitromethyl, hydroxymethyl, alkoxymethyl where alkoxy contains 1 to 6 carbon atoms, carboxymethyl, carbalkoxymethyl, bis(carboxy)methyl, bis(carbalkoxy)methyl, cyanomethyl or halomethyl.

11. A compound according to claim 1 wherein:
  X is O or S;
  n has a value of 4 to 8;
  $R_1$ is hydrogen, alkyl or aralkyl of up to 12 carbon atoms;
  $R_2$ is hydrogen, alkyl of 1 to 4 carbon atoms, or phenyl;
  $R_3$ is hydroxy, alkanoyloxy of 1 to 4 carbon atoms or benzyloxy;
  $R_4$ is hydrogen, alkyl of 1 to 9 carbon atoms, cycloalkyl of 5 to 8 carbon atoms, phenyl, naphthyl, alkyl of 1 to 6 carbon atoms substituted with phenyl, naphthyl or cycloalkyl of 5 to 8 carbon atoms, any of said phenyl rings or naphthyl rings being unsubstituted or substituted with halo, trifluoromethyl, alkyl of 1 to 6 carbon atoms, alkoxy of 1 to 6 carbon atoms or nitro;
  $R_5$ is alkyl of 1 to 6 carbon atoms, phenyl, phenylalkyl wherein alkyl contains 1 to 6 carbon atoms, carboxy or carbalkoxy wherein alkoxy contains up to 12 carbon atoms.

12. A compound according to claim 11 wherein n is 5, 6 or 7.

13. A compound according to claim 11 wherein $R_3$ is hydroxy.

14. A compound according to claim 11 wherein $R_4$ is alkyl of 1 to 9 carbon atoms.

15. A compound according to claim 11 wherein $R_5$ is alkyl of 1 to 6 carbon atoms.

16. A compound according to claim 11 wherein:
  n is 5, 6 or 7;
  $R_2$ is hydrogen, methyl, ethyl or phenyl;
  $R_3$ is hydroxy;
  $R_4$ is hydrogen or alkyl of 1 to 9 carbon atoms;
  $R_5$ is alkyl of 1 to 6 carbon atoms, phenyl, phenylalkyl wherein alkyl contains from 1 to 6 carbon atoms, carboxy or carbalkoxy wherein alkoxy contains up to 12 carbon atoms.

17. A compound according to claim 16 wherein X is O.

18. A compound according to claim 16 wherein $R_1$ is hydrogen or alkyl of 1 to 6 carbon atoms.

19. A compound according to claim 16 wherein $R_2$ is hydrogen.

20. A compound according to claim 16 wherein $R_2$ is methyl.

21. A compound according to claim 16 wherein $R_4$ is alkyl of 4 to 9 carbon atoms.

22. A compound according to claim 21 wherein $R_4$ is n-pentyl, n-hexyl or n-heptyl.

23. A compound according to claim 22 wherein $R_4$ is n-hexyl.

24. A compound according to claim 21 wherein $R_4$ is hex-2-yl, hept-2-yl or oct-2-yl.

25. A compound according to claim 16 wherein $R_5$ is alkyl of 1 to 6 carbon atoms.

26. A compound according to claim 25 wherein $R_5$ is methyl.

27. The sodium salt of a compound according to claim 16 wherein $R_1$ is hydrogen.

28. 1-(3'-Hydroxy-3'-methyl-n-nonyl)-3-methyl-5-(6''-carboxy-n-hexyl)hydantoin.

29. The compound according to claim 1 which is 1-(3-hydroxy-3-methyl-n-nonyl)-3-cyanomethyl-5-(6-carbomethoxy-n-hexyl)hydantoin.

30. The sodium salt of the compound of claim 28.

31. A pharmaceutical composition for effecting a prostaglandin-like response comprising an effective amount of a compound according to claim 1 and a pharmaceutically acceptable carrier.

32. The method of effecting a prostaglandin-like response in humans and other animals which comprises administering thereto an effective amount of a compound according to claim 1.

* * * * *